United States Patent [19]

Thomte

[11] 4,403,517
[45] Sep. 13, 1983

[54] LIQUID SAMPLING

[75] Inventor: Magnus Thomte, Oslo, Norway

[73] Assignee: Interpower A/S, Oslo, Norway

[21] Appl. No.: 270,541

[22] Filed: Jun. 4, 1981

[30] Foreign Application Priority Data

Jun. 6, 1980 [NO] Norway .................................. 801702

[51] Int. Cl.³ .............................................. G01N 1/14
[52] U.S. Cl. .............................. 73/863.84; 73/863.31; 73/863.43
[58] Field of Search ........... 73/863.02, 863.31, 863.43, 73/863.84, 864.34

[56] References Cited

U.S. PATENT DOCUMENTS 1,693,359 11/1927 Gard .
2,693,114 11/1954 Tapp et al. ........................ 73/863.02
2,979,956 4/1961 Warren .............................. 73/863.83
3,031,890 5/1962 Struck ............................... 73/863.84
3,090,323 5/1963 Smith .
3,160,016 12/1964 Middleton ......................... 73/863.43
3,184,973 5/1965 Bradley .
3,229,527 1/1966 Johnson .
3,949,613 4/1976 Irwin .
4,009,617 3/1977 Johnson .

OTHER PUBLICATIONS

True-Cut proportionate fluid sampler, An advertising brochure from True-Cut Products Inc., Santa Barbars Airport, Goleta CA.
Gibson–Oil & Gas Journal, vol. 52, No. 39, Feb. 1, 1954 pp. 68 & 69.
North, New Device Will Aid Oil Sampling, Lloyds List Mar. 4, 1981 1 page.
Scandanavian Oil Gas Magazine, Mar./Apr. 1981 p. 39.
A Programme for Fuel Quality Testing, published by Det Norske Veratas, 11 pages.
Guidlines for Fuel Sampling, published by Det Norske Veratas 5 pages.

*Primary Examiner*—S. Clement Swisher
*Attorney, Agent, or Firm*—William R. Hinds

[57] ABSTRACT

Apparatus for the sampling of heavy fuel oil supplied to a ship as bunker fuel consists of a pipe section for oil flow containing a static vane mixer, and a positive displacement pump with its inlet communicating with the interior of the pipe section downstream of the mixer, together with a delay timer causing the pump to pump out a small quantity of oil at regular intervals into a receptacle where these extracted quantities accumulate progressively during the course of the bunkering period.

10 Claims, 9 Drawing Figures

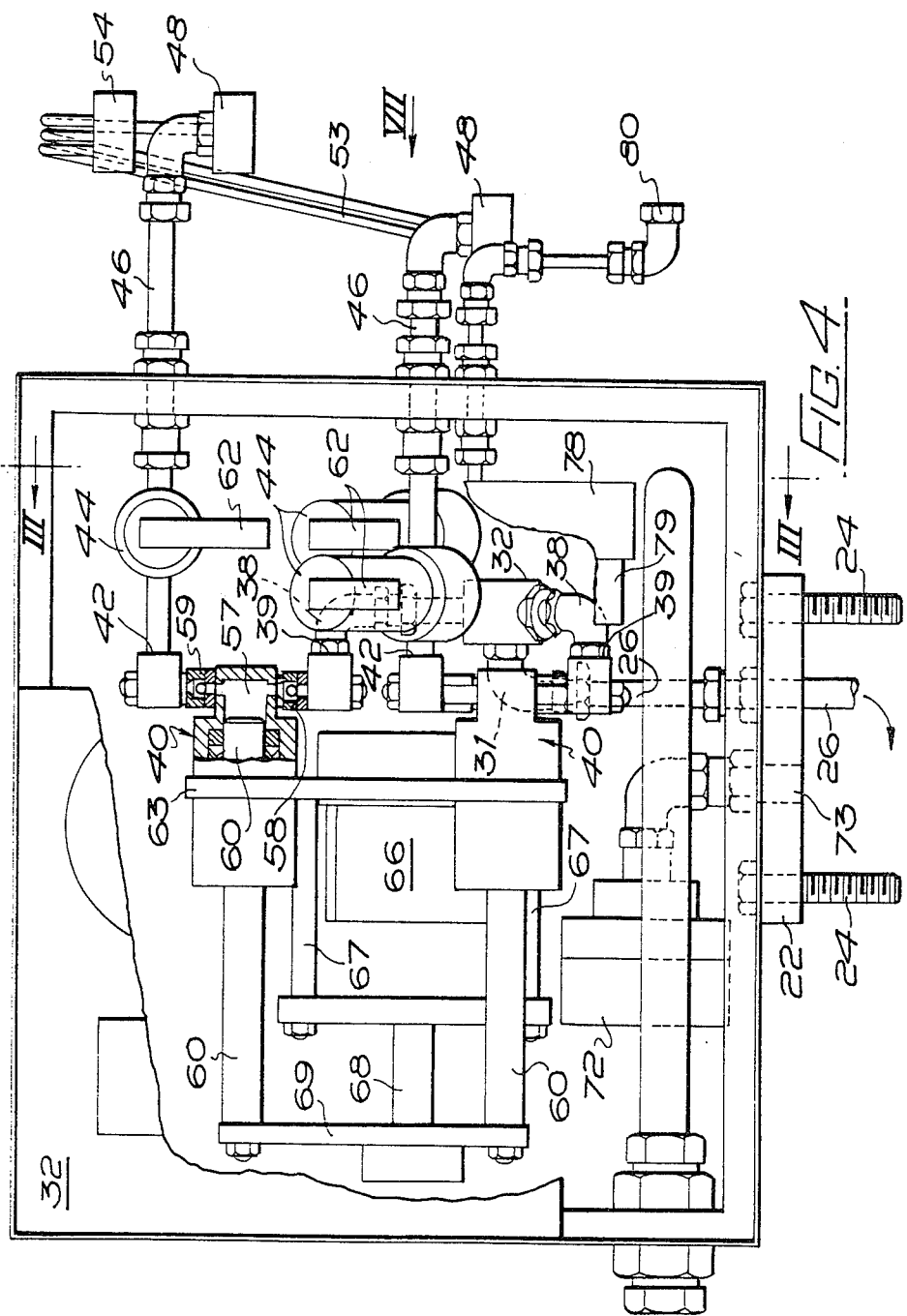

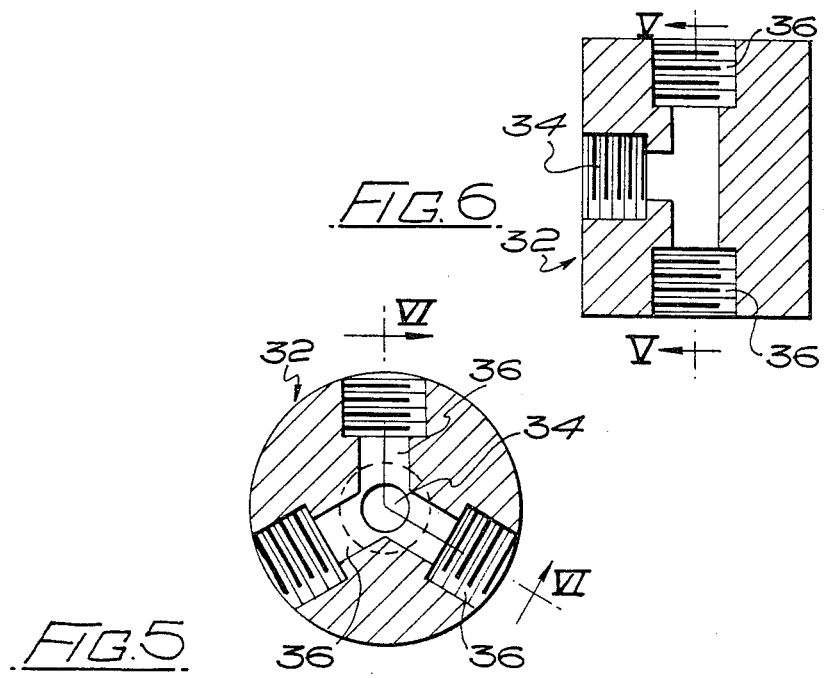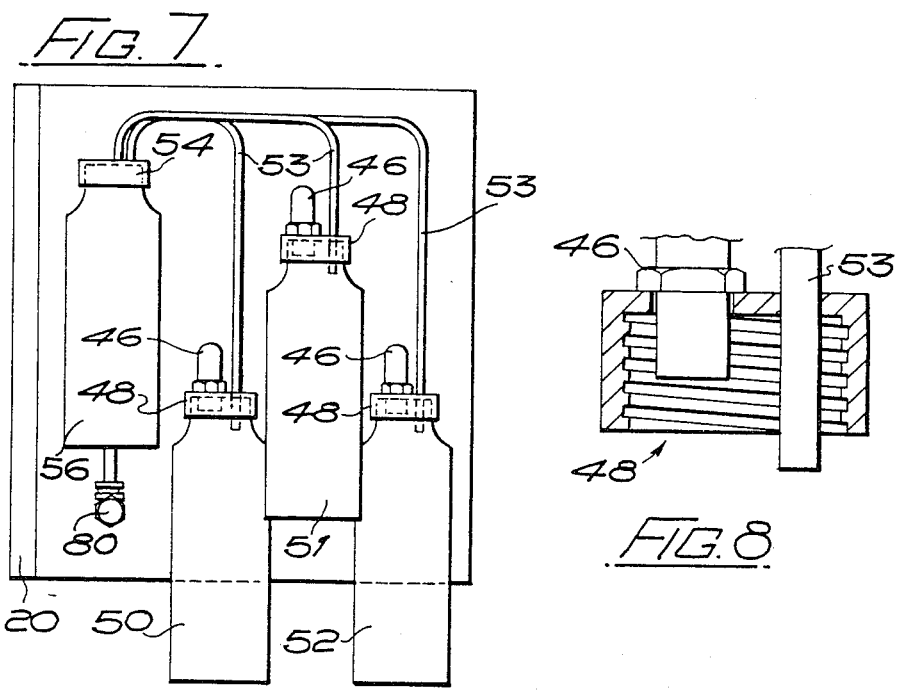

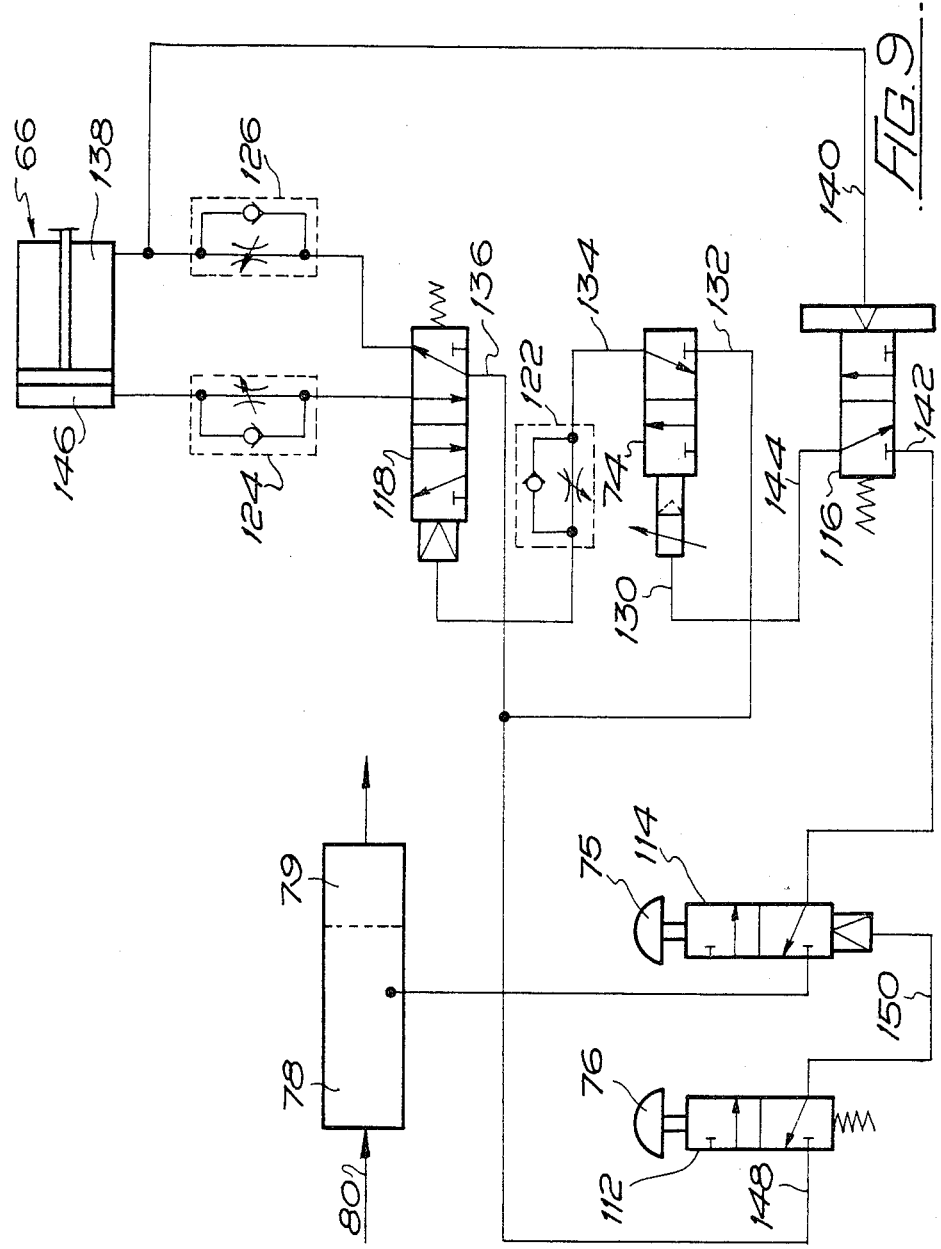

LIQUID SAMPLING

BACKGROUND OF THE INVENTION

This invention relates to the sampling of liquid which is being delivered along a flow path. The invention is applicable to a variety of circumstances and liquids, especially viscous liquids. Hydrocarbon mixtures such as bunker fuel, lubricating oil or crude oil are notable applications. The use of the invention which is particularly envisaged is in sampling heavy fuel oil which is being supplied to a ship as bunker fuel for the ship's engine(s).

Heavy fuel oil is a very viscous material, and because of this it is customarily supplied through heated hoses at a temperature of 55° C. and a pressure of about 8 bar.

With rising crude oil prices the quality of heavy fuel oil has rapidly deteriorated. An inadequate quality of fuel oil can lead to excessive engine wear and/or breakdown. For instance an excessive content of high boiling materials creates incomplete combustion resulting in deposits which will tend to clog piston ring clearances. Another effect is ignition delays resulting in higher oil film stresses. Catalytic fines, originating from catalytic cracking processes can sometimes be found in heavy fuel oil and are an abrasive contaminant which can lead to engine breakdowns.

The damage resulting from bad quality fuel may well be difficult to attribute to the supplier of that fuel, because of the difficulty in proving when and where the fuel in question was taken on board. Prior to this invention it was not unusual to take samples of bunker fuel for analysis but such samples were usually taken only at the beginning and/or the end of the bunkering operation. It is possible for such samples to give a satisfactory analysis even though a substantial quantity of contaminants have in fact been included in the oil supplied, because the quality of that oil has varied during the course of the bunkering operation. For instance, water may be pumped on board during a relatively short part of the bunkering operation, perhaps as the supplier empties a tank.

SUMMARY OF THE INVENTION

Broadly in this invention small quantities are extracted from the flow which is being delivered through the pipe over the course of delivery, and these quantities are accumulated to provide a representative sample of the oil or other liquid delivered. The small quantities may be extracted at regular intervals under the command of a delay timer. Preferably such a delay timer is made adjustable so that the same total volume of sample can be collected from bunkering operations of various durations. As an alternative to timed intervals it would be possible to govern the rate at which small quantities were removed in proportion to the rate of flow which was being delivered. It is considered, however, that this would lead to an undesirable degree of complexity and high cost of manufacture of the apparatus, and the use of regular time intervals is preferred.

Preferably, the flow through the pipe is mixed and the small quantities are extracted from just downstream of the mixing operation. This enables a very representative sample to be obtained.

The invention also provides apparatus for sampling liquid which is being delivered through a pipe from a supply to at least one receiving container, which apparatus comprises a pump having its inlet connected or connectable to the interior of the pipe and has its outlet connected to a connector to which there can be attached a receptacle in which the sample is progressively accumulated.

It is strongly preferred to use a positive displacement pump. Such a pump has an operating cycle in which a definite volume is pumped, and so will have a constant delivery rate even if there are large variations in viscosity. Since the flow rate through the pipe during bunkering is more or less constant the apparatus will consume a proportional part of the quantity loaded and provide a representative sample of the total fuel volume bunkered. The apparatus preferably includes a pipe section through which the flow to be sampled is passed, which includes within it a static vane mixer to mix the liquid as it flows through the pipe, and which has an opening through which a sampling tube connected to the pump inlet communicates with the interior of the pipe section downstream of the mixer. The pipe section and the remainder of the apparatus can be constructed as a portable unit which can be stored under cover when not in use. For use the pipe section can be interposed between the supply hose and the pipework of the ship to which the hose would normally be connected. In this way the pipe section becomes incorporated as part of the pipe through which flow takes place. Alternatively, and rather better, the pipe section can be incorporated in the pipework inboard of the point to which the supply hose is attached.

It is preferred to accumulate each sample over the whole of a bunkering or other delivery period in order not to have to mix the contents of more than one sample receiver in order to get a representative sample. If the bunker fuel which is supplied is loaded into a plurality of separate tanks in a vessel, and these are loaded in succession, it is desirable to take a sample for each separate tank. Then if the quality of the bunker fuel varies so that one tank is loaded with a poorer quality than the others, this tank can be isolated when the analysis results are received, whereas the contents of the other tanks will be known to be satisfactory and can be used without risk.

The preferred embodiment described hereinafter is intended to collect three identical samples of bunker fuel supplied to a ship. One sample would be sent for analysis, one handed to a representative of the suppliers and the third retained on the ship or by some other representative of the ships owners. All of these samples would desirably be collected over the whole bunkering period, or if appropriate all of them collected during the loading of one separate tank, and three more collected during the loading of each successive tank.

While the invention is particularly envisaged in connection with bunker fuel, it could also be employed for sampling the lubricating oil for the ship's main engine. The main engine of a large ship requires several tons of lubricating oil which therefore represents a considerable value and can give rise to substantial engine damage if it is of bad quality or to the wrong specification. The invention can also be employed for sampling the cargo of crude oil taken onto a tanker in order to have samples which can be used for deciding any disputes regarding the quality of the cargo prior to delivery.

BRIEF DESCRIPTION OF THE DRAWINGS

FIG. 4 is a section on the line IV—IV of FIG. 3, partly cut away and with most pneumatic components again being omitted;

FIG. 5 is a vertical section through the distribution block on line V—V of FIG. 6;

FIG. 6 is a section on line VI—VI of FIG. 5;

FIG. 7 is an end view of the unit and collecting bottles seen in the direction of arrow VII of FIG. 4;

FIG. 8 is a section through a connector for a bottle;

FIG. 9 is a diagram showing the pneumatic circuit.

DESCRIPTION OF PREFERRED EMBODIMENT

Figure 1:
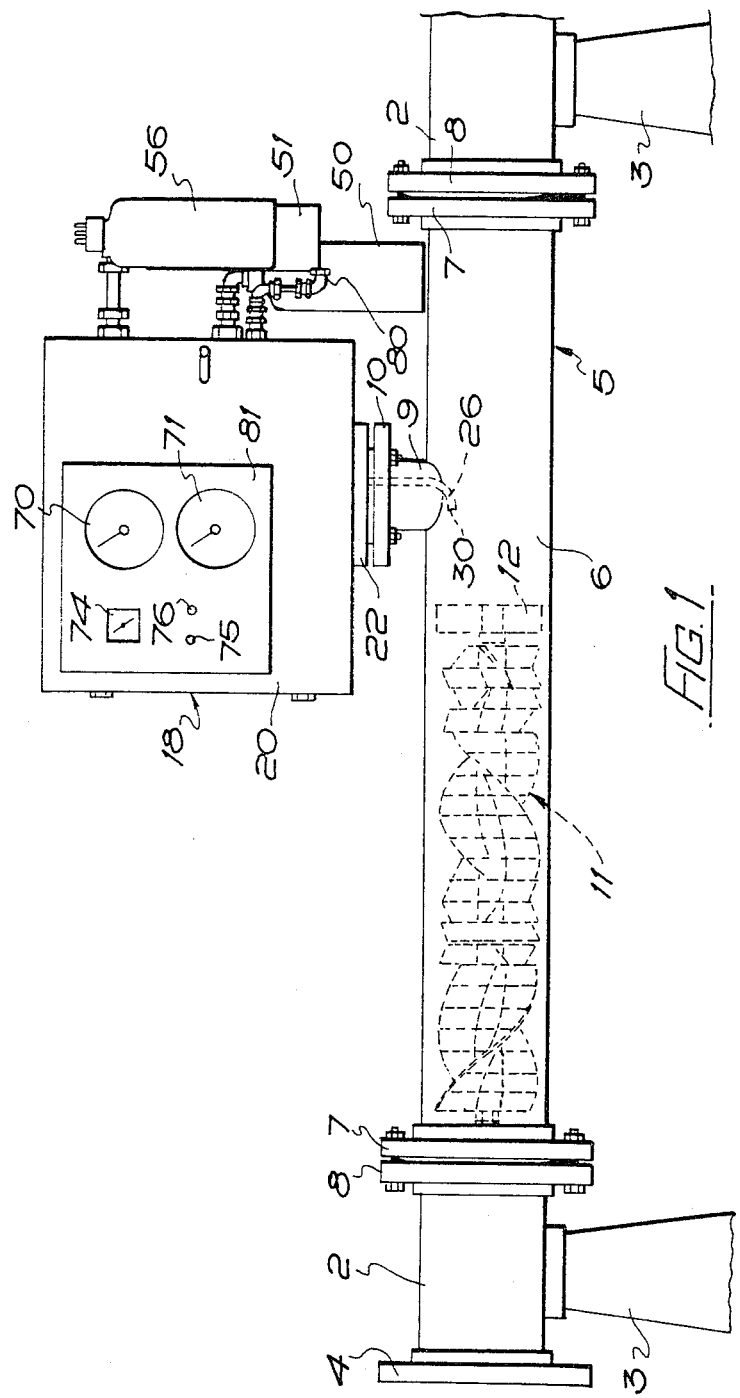
FIG. 1 shows a spool piece and portable unit attached thereto embodying this invention and incorporated in fixed pipe-work.
Figure 2:
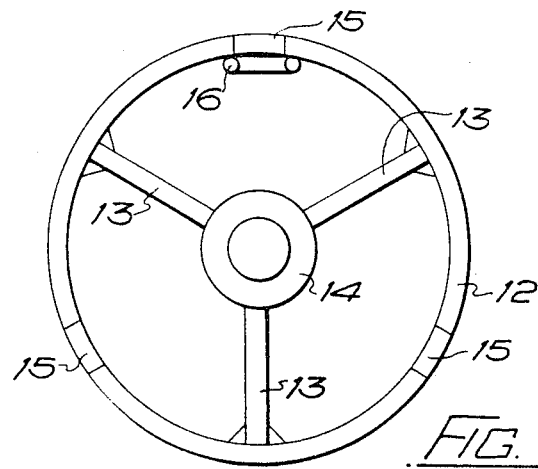
FIG. 2 shows a retaining ring for the static vane mixer.

Reference will first be made to FIGS. 1 and 2 of the drawings. A ship typically is provided with a plurality of bunker points, such as one in a forward position at each side of the vessel and one in an aft position at each side. At each bunker point there is fixed pipework 2 supported on substantial cradles 3 and terminating in an end flange 4 some two meters from the ship's side, and to which a supply hose from a jetty or bunkering barge can be attached.

For the sampling of bunker oil as it is delivered onto the ship, a spool piece as shown by FIG. 1 is permanently inserted at each bunker point in place of an equivalent length of the existing pipework, slightly inboard of the flange to which the supply hose can be attached.

The spool piece 5 shown in FIG. 1 consists of a pipe section 6 provided at each end with mounting flanges 7 by which it is bolted to flanges 8 welded to the pipework 2 at either side. It has a radial access port 9 terminating in a mounting flange 10. The spool piece is mounted so that the access port 9 faces upwardly.

Within the pipe section a static vane mixer 11 is fitted. This is an assembly of fixed blades which cause turbulence in the oil as it flows past them and so mixes the oil by causing different parts of the flow to shear against each other. The purpose of this mixer is to give uniformity of composition across the whole cross section of flow at the region 12 immediately downstream of the mixer. It is from here that samples are taken.

Static vane mixers are known pieces of equipment and a suitable mixer is available from Lightnin Mixers Limited, Stockport, England, under their brand name "Inliner".

The static vane mixer 11 is a fairly close fit in the pipe section 6 and it is retained against the thrust applied to it by the oil flow by means of an assembly as illustrated in FIG. 2. This consists of a ring 12 whose outer diameter matches the internal diameter of the pipe section 6, three radial vanes 13 carried by this ring and supporting a central hub 14. The positioning ring is fixed in place in the spool piece. The static vane mixer 11 has a central shaft whose downstream end is received in the hub 14. The downstream vanes of the mixer engage slots 15 in the upstream face of the ring 12 and one of these vanes is secured to a U bolt 16 welded to the ring 12; in this way rotation of the mixer 11 is prevented.

When a bunkering point is not in use its opening 9 will be closed off by a blank plate (not shown) bolted to its flange 10. Before bunkering is commenced the portable sample unit 18 illustrated by FIG. 2 onwards is fitted to the spool piece 5 at whichever bunker point is to be used. The unit 18 has a generally cuboidal cabinet with a circular plate 22 and mounting bolts 24 rigidly attached to its underside. Its front face is a door 20 giving access to the cabinet interior. After the blank plate has been removed from the flange 10 of the appropriate spool piece 5, the portable unit 18 is fitted onto the flange to take the position shown in FIG. 1. The bolts 24 of the unit allow it to be secured to the bolt holes in the flange 10.

Figure 3:
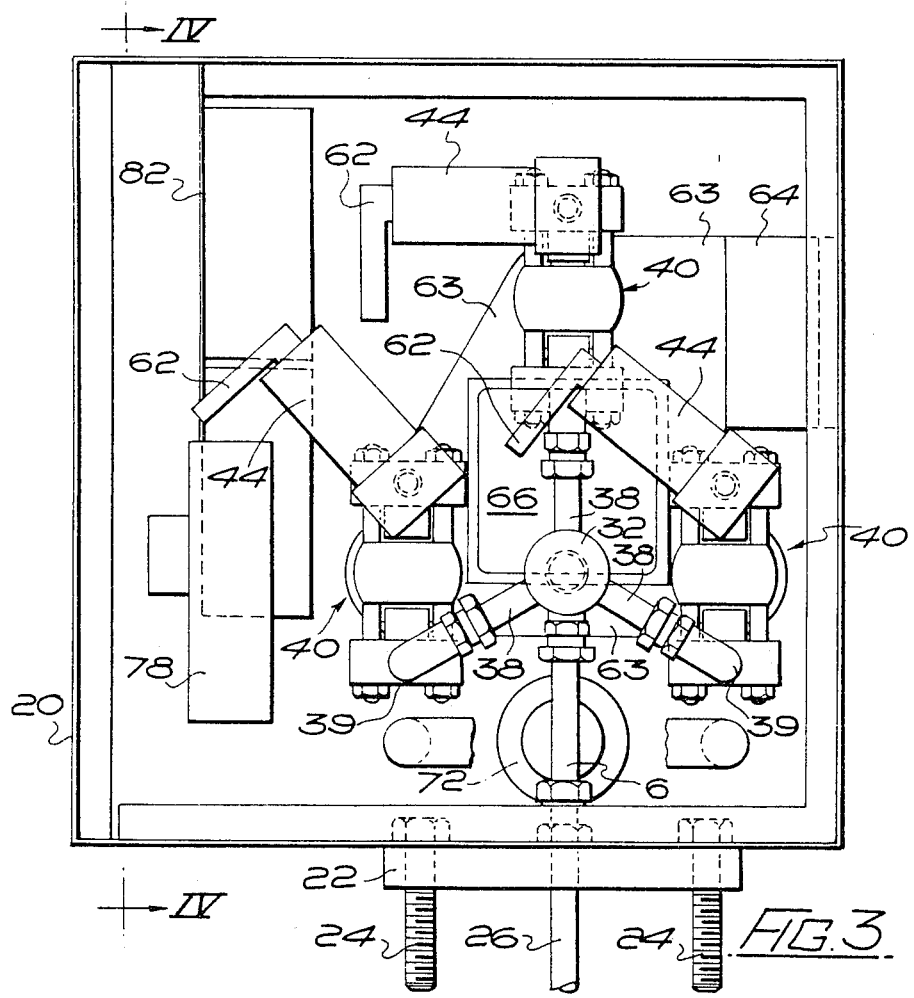
FIG. 3 is a section through the unit on line III—III of FIG. 4, omitting most pneumatic components and showing the pumps in end elevation.

Turning now to FIG. 3 onwards of the drawings, the portable unit 18 has a sampling tube 26 projecting from its underside. This tube 26 is led sealingly through the plate 22 and has a curved bottom end portion so that its open end 30 is exposed to the oncoming flow of oil downstream of the mixer. The sampling tube 26 leads upwards to an elbow 31 connecting it to a cylindrical distribution block 32 which has a central inlet 34 communicating with three radial outlet passages 36 (FIGS. 5 and 6). Respective pipes 38 lead from the passages 36 to the inlets 39 of three positive displacement pumps 40. The outlets 42 of these positive displacement pumps are connected to pressure retaining valves 44 (shown in phantom). These in turn are connected by pipes 46, which lead through the end face of the cabinet 20, to respective screw connectors 48 into which the necks of three collecting bottles 50,51,52 can be screwed. Each of the fittings 48 also has a tube 53 which leads vented air, or overflowing oil when the bottle is full, to a fourth connector 54 onto which a fourth bottle 56 is screwed to receive any overflow. The connector 54 has a hole venting to atmosphere. The positions of the bottles relative to the spool piece 5 are indicated in FIG. 1. Although not so shown, the overflow bottle 56 could be made somewhat larger than the other three bottles.

One pump 40 is shown partially sectioned in FIG. 4. Its body defines a working chamber 57 separated from the inlet through non return valves 58,59. A piston 60, sliding through seals 61, enters the chamber 57. When the piston is urged to the left, as seen in FIG. 4, oil is drawn in through valve 58. When the piston moves to the right the oil is expelled through valve 59 to the outlet 42.

The pressure retaining valves 44 are provided because the bunker oil is delivered under a pressure of 8–10 bar, and if the pumps 40 delivered only against atmospheric pressure their volumetric characteristics could be affected so that they did not deliver the proper amount. The valves 44 are set to provide a back pressure of 10 bar, to ensure that the pumps 40 deliver against a higher pressure (i.e. they are actually pumping). Each valve 44 has an operating handle 62 for removing the back pressure while the system is initially primed. Suitable pumps 40 and pressure retainers 44 are available from Wallace and Tiernan Limited, Tonbridge, England under their part numbers 33606A and 33668D.

The pumps 40 are mounted on a plate 63 welded to a bracket 64 attached to the rear of the cabinet.

The pistons 60 of the pumps 40 could each be driven by a separate pneumatic cylinder. However, to ensure that all three pumps operate to an identical extent, the three pistons 60 of the pumps are driven by a single cylinder 66. The cylinder 66 is attached to the plate 63 by bolts 67 (not shown in FIG. 3) so as to be fixed in relation to them, and disposed between them. The piston 68 of the cylinder 66 is attached to a plate 69 to which the pistons 60 are all attached. Operation of the cylinder 66 thus moves all three pistons 60 simultaneously and to an equal extent causing identical operation of all three pumps 40.

The portable unit 18 is provided with a thermometer 70 to indicate the temperature in the cabinet, a pressure gauge 71 to indicate the pressure of the bunker oil in the spool piece, and controls for the operation of the pneumatic cylinder 66. The pressure gauge 71 is connected by a capilliary (not shown) filled with silicone oil to a diaphragm seal unit 72 which is connected to a second hole 73 through the plate 22 and thus is exposed to the pressure within the spool piece 5.

The operation of the cylinder 66 is governed by a pneumatic control system. This employs a pneumatic delay timer 74 which causes operation of the cylinder 66 and hence the pumps 40 each time it is required to withdraw a small quantity of oil from the flow through the spool piece 5. Start and stop buttons 75, 76 are provided, governing the supply of air to the timer 74. The pneumatic equipment, including a combined filter and pressure regulator 78 and a lubricator 79 for the incoming air, is mounted just inside the front face of the cabinet 20. An inlet 80 is provided on the cabinet for connection to the ship's supply of compressed air. The timer 74, the start and stop buttons 75, 76 and the gauges 70, 71 are visible through a window 81 in the door at the front of the cabinet. These, and many pneumatic components (not shown) are mounted on a plate 82 on the inside of the cabinet 18.

The pneumatic circuit is shown diagrammatically in FIG. 9. The air inlet 80 is connected to a filter and pressure regulator which is connected through a lubricator to various valves. The pneumatic circuit employs a push button operated spring returned valve 112, a push button operated pneumatically returned valve 114, a spring returned poppet valve 116, a pneumatically operated spring returned spool valve 118, a pneumatic delay timer 74 and three flow control valves 122, 124 and 126 each of which comprises a non return valve permitting free flow in one direction and an adjustable restricted by-pass permitting return flow past the non return valve, but restricting the rate of such return flow. All of these parts are conventional components.

The pneumatic timer is driven by a supply of air entering it at 130 and, driven by this air, the valve which is incorporated in it periodically moves over against its return spring so as to connect port 132 to line 134. It remains there until port 130 is vented. The timer is adjustable by means of an operating knob to vary the delay before its valve moves over against the return spring. Suitable pneumatic timers are made by H. Kuhnke Ltd., Penn, Bucks, England.

The circuit functions as follows:

Once the ships air supply has been connected to the inlet 80, the apparatus assumes its normal rest state. Air admitted at port 136 of valve 118 passes through flow control valve 126 to pressurise chamber 138 of the main pneumatic cylinder and also, via line 140 to maintain the poppet valve 116 pushed over against its return spring so that its inlet port 142 is connected to line 144 leading to port 130 of the timer.

The apparatus will remain static in this condition indefinitely until the start button 75, which is the operating button of valve 114, is pressed, to connect a supply of air from the regulator to port 142 of valve 116 and thence via line 144 to the pneumatic timer. After the interval determined by the timer has elapsed the valve in the timer changes over and air from port 132 is admitted via line 134 to operate spool valve 118. Valve 118 functions as the pneumatic equivalent of an electrical relay. When operated it disconnects the supply of air entering its port 136 from the chamber 138 of the cylinder and instead connects it via flow control 124 to chamber 146 of the cylinder. The chamber 146 is thus pressurised, so driving the piston of the cylinder through its operating stroke. Air from the chamber 138 exhausts through the flow control 126, which is set to allow a high rate of flow. As the chamber 138 vents so also does the operating cylinder of the poppet valve 116 until it is returned by its spring, so cutting off the supply of air to the inlet 130 of the timer and instead venting via line 144. This enables the return spring in the timer to restore the position of the valve in it, thus resetting the timer.

The supply of air to drive over the spool valve against its return spring has now been cut off and the return spring thus returns the valve, but this action is rather slow, however, because the flow control 122 is set to permit only a low rate of flow. Thus return of the valve 118 is delayed sufficiently long for the stroke of the piston in the main operating cylinder to be completed and allow the timer to be fully reset. When the valve 118 is returned by its spring, chamber 138 is again pressurised to return the piston, and air is also admitted to line 140 to operate the poppet valve 116.

Thus the rest condition of the circuit has been restored and air is again being supplied to the inlet 130 of the timer, so that a further interval is being timed. The circuit will continue to move at regular intervals in this way, until such time as it is stopped by depressing the stop button 76 which operates valve 112 against its return spring to admit air from port 148 via line 150 to return the start valve 114 and so cut off the supply of air to inlet 130 of the timer.

Suitable controlled flows through the valves 122, 124 and 126, by passing their non return valves, are 3 c.f.h., 14 c.f.h., and 65 c.f.h. respectively, all at 3.5 bar. The pneumatic circuit would then require a minimum air supply of 20 c.f.h. at 3.5 bar.

Use of the portable unit 18 is as follows. As already explained, the unit would be fitted onto the flange 10 at the bunkering point which was to be used, before bunkering begins. When flow starts the pressure shown on the gauge will rise to some 8 or 10 bar. The operating handles 62 of the pressure retaining valves 44 are then opened to prime the pumps 40. The handles 62 are kept open—and the pumps 40 operated if necessary—until oil appears at each of the connectors 48. They are then turned back so that the pumps thereafter deliver against pressure imposed by the retaining valves 44.

The pipes 46 may be transparent, in which case it will only be necessary to keep the handles 62 open until oil is seen in these pipes. When the pumps 40 have been primed, collecting bottles 50, 51, 52 and 56 are screwed onto their respective fittings 48, 54 and the pneumatic timer set so as to cause the withdrawal of oil at the intervals required.

The quantity of oil which is withdrawn each time is determined by the capacity which each pump 40 delivers in one operating cycle. The sampling interval is chosen, taking the pump capacity into account, so that the collecting bottles will just be filled during the expected length of the bunkering period. For example if the pumps each displace 12 ml in one operation, the ship is expected to bunker for four hours and it is desired to collect one liter in each of the three sample bottles, then the pneumatic timer will be set so that the sampling operation takes place every 2.9 minutes.

When bunkering is completed the portable unit is turned off and the three sample containers 50,51,52 are removed, fitted with screw caps, and labelled. One would then be handed to a representative of the oil supplier, one would be retained by the ship or other representative of the ship's owners, and the third sent for analysis.

It is desirable with heavy fuel oil that the portable unit 18 should be cleaned out by steam cleaning after use. The ability to remove it from the spool piece enables this to be done in the ship's engine room where it will readily be possible to blow steam through it, followed by dry air. It will also be possible to store it under cover.

Because heavy fuel oil is very viscous at room temperature it is customarily supplied to a ship through heated hoses and at some 55° C. It may therefore be necessary to provide heating within the portable unit 18 if bunkering is taking place at a cold ambient temperature. To enable this a U-tube through which steam can be passed may be provided as indicated at 84. Also, as shown the cabinet is of a double skinned construction with insulation (not shown) between the skins. The door 20 is not shown double skinned, but could be given a double skinned construction if desired. The double skinned construction assists in maintaining the cabinet interior at a temperature at which the oil will flow, even under cold environmental conditions.

I claim:

1. Portable apparatus for sampling viscous oil delivered through a pipe from a supply to at least one receiving container on board a ship, comprising
   a portable structure,
   a positive displacement pump having an inlet and an outlet,
   an inlet duct for communicating the pipe interior with said pump inlet,
   a connector for attaching a sample collecting receptacle,
   a further duct connecting said pump outlet to said connector,
   drive means for said pump, and
   control means arranged to operate said drive means and hence said pump, to extract small quantities over the course of delivery and supply them to the collecting receptacle to accumulate therein, said pump, connector, further duct, drive means and control means being assembled to said structure, whereby the assembly thereof is portable as a self-contained unit for ready connection to and disconnection from the pipe so as to permit ready connection for use with said assembly disposed exteriorly of said pipe, and said inlet duct connecting said pipe interior to said pump inlet, and also to permit disconnection for storage during periods of nonuse.

2. Apparatus according to claim 1 wherein said control means comprises a delay timer to operate said drive means at regular intervals, said timer being adjustable to vary the duration of said intervals.

3. Apparatus according to claim 2 wherein said drive means is a pneumatic actuator and said control means is pneumatic.

4. Portable apparatus according to claim 1, wherein said portable structure comprises a casing enclosing at least said pump, said drive means and said control means, manually operable controls to start and stop said drive means being provided on the exterior of said casing.

5. In combination, portable apparatus according to claim 1, and a pipe section for incorporation into said pipe, the combination including means for connection of said inlet duct to the interior of said pipe section through a lateral opening in said pipe section.

6. The combination of claim 5 including means for mounting the portable apparatus on the pipe section with said inlet duct communicating with the interior of said pipe section.

7. The combination of claim 5 wherein a sampling tube projects into the interior of the pipe section and terminates at an open end facing the oil flow and spaced from the walls of the pipe section.

8. The combination of claim 5 further including a static vane mixer in said pipe section to mix liquid flowing therethrough, said lateral opening being downstream of said mixing means.

9. In combination, a ship having pipework to receive viscous oil from a supply and deliver it to at least one or more tanks on board the ship, portable apparatus according to claim 1, and a pipe section incorporated into said pipework, which section has a lateral opening for connection of said inlet duct to the interior of said pipe section through said lateral opening.

10. The combination of claim 9 wherein said pipework includes at least one connection point for attachment of a flexible hose from said supply, and a said pipe section proximate each said connection point, each said connection point and pipe section proximate thereto being exposed on deck.

* * * * *